US 011793913B2

(12) United States Patent
Boddie et al.

(10) Patent No.: US 11,793,913 B2
(45) Date of Patent: Oct. 24, 2023

(54) BREAST PUMPING SYSTEM

(71) Applicant: RESTFUL PUMP, INC., Pembroke, MA (US)

(72) Inventors: Micolene Boddie, Lakeville, MA (US); Blake Sama, Boston, MA (US)

(73) Assignee: RESTFUL PUMP, INC., Pembroke, MA (US)

( * ) Notice: Subject to any disclaimer, the term of this patent is extended or adjusted under 35 U.S.C. 154(b) by 528 days.

(21) Appl. No.: 16/851,706

(22) Filed: Apr. 17, 2020

(65) Prior Publication Data

US 2021/0121615 A1    Apr. 29, 2021

Related U.S. Application Data

(63) Continuation-in-part of application No. 16/665,448, filed on Oct. 28, 2019.

(51) Int. Cl.
| | |
|---|---|
| *A61M 1/06* | (2006.01) |
| *A47C 7/62* | (2006.01) |
| *A47C 9/00* | (2006.01) |

(52) U.S. Cl.
CPC ............ *A61M 1/064* (2014.02); *A47C 7/622* (2018.08); *A47C 9/005* (2013.01)

(58) Field of Classification Search
CPC ........ A61M 1/06; A61M 1/062; A61M 1/064; A61M 1/066; A61M 1/067; A61M 1/068; A61M 1/069
See application file for complete search history.

(56) References Cited

U.S. PATENT DOCUMENTS

| | | | |
|---|---|---|---|
| 78,472 | A | 6/1868 | Neuhaus |
| 4,552,404 | A | 11/1985 | Congleton |
| 4,589,699 | A | 5/1986 | Dungan |
| 5,149,174 | A | 9/1992 | Charash |
| 5,667,278 | A | 9/1997 | Li |
| 6,502,262 | B1 | 1/2003 | Piscopo |
| 7,070,241 | B2 | 7/2006 | Saulnier et al. |
| 7,540,049 | B2 | 6/2009 | Sklenarik et al. |
| 7,784,871 | B2 | 8/2010 | Cochran |
| 8,043,255 | B2 | 10/2011 | Weston |
| 8,590,968 | B2 | 11/2013 | Zahir |

(Continued)

FOREIGN PATENT DOCUMENTS

| | | |
|---|---|---|
| CN | 203280090 | 11/2013 |
| WO | 2003/013628 | 2/2003 |

(Continued)

OTHER PUBLICATIONS

Patent Cooperation Treaty, Notification of Transmittal of the International Search Report and the Written Opinion of the International Searching Authority, or the Declaration, dated Jan. 28, 2021.

*Primary Examiner* — Dung T Ulsh
(74) *Attorney, Agent, or Firm* — Troutman Pepper Hamilton Sanders LLP (Rochester)

(57) ABSTRACT

A breast pumping assembly for a forward-leaning chair is provided. The assembly allows for a breast pumping mother to be optimally positioned and comfortable while pumping breast milk, leading to quicker and more effective pumping. The breast pumping assembly and the chair are adjustable to adapt for different sized mothers and changing body size and shape as pumping progresses.

10 Claims, 12 Drawing Sheets

(56) References Cited

U.S. PATENT DOCUMENTS

| | | |
|---|---|---|
| 9,138,072 B1 | 9/2015 | Sanders |
| 9,480,783 B2 | 11/2016 | Johnson et al. |
| 2005/0235425 A1 | 10/2005 | Parrilla |
| 2006/0265809 A1* | 11/2006 | Wagner ................ A47D 13/083 5/655 |
| 2007/0135761 A1* | 6/2007 | Cheng .................. A61M 1/062 604/74 |
| 2009/0211584 A1* | 8/2009 | Savich .................. A61G 13/12 128/845 |
| 2010/0194166 A1 | 8/2010 | Grenier |
| 2011/0315832 A1 | 12/2011 | Box |
| 2012/0260831 A1 | 10/2012 | McCarty |
| 2019/0151520 A1* | 5/2019 | Fisher .................. A61M 1/062 |

FOREIGN PATENT DOCUMENTS

| | | | |
|---|---|---|---|
| WO | WO-2008085174 A1 * | 7/2008 | ........... A47C 15/004 |
| WO | 2009044422 | 4/2009 | |
| WO | 2018/060698 | 4/2018 | |

* cited by examiner

BREAST PUMPING SYSTEM

BACKGROUND

Technical Field

The present disclosure relates generally to breast pumping systems. More particularly the present disclosure relates to an assembly which allows a mother to lean forward in a relaxed position while using a breast pump to pump breastmilk.

Description of Related Art

Feeding infant children using breastmilk has a number of advantages from both a health, financial, and convenience perspective. In many instances, to build up a store of milk for feeding the infant, mothers will pump milk for later consumption. This advantageously allows a mother to return to work, and be away from the infant for periods of time.

However, many mothers struggle with nursing for many reasons, including providing enough milk volume to feed the growing child. This is a very common issue with various causes. Some causes of milk production shortages include stress and anxiety of caring for the infant, discomfort caused by nursing and pumping, and discomfort from the various body positions that must be maintained for extended periods of time during a pumping session. Often, during a pumping session, a woman is seated with poor posture. This can lead to sub-optimal positioning, leading to inefficient pumping, less milk extraction, and reduced milk production.

Therefore, what is needed is breast pumping system which can allow a mother who is pumping breastmilk to rest in a comfortable and physiologically ideal position.

SUMMARY

The subject matter of this application may involve, in some cases, interrelated products, alternative solutions to a particular problem, and/or a plurality of different uses of a single system or article.

In one aspect, a breast pumping assembly is provided which is attachable to a forward-leaning chair. The assembly comprises a breast pumping table and a bottle shelf positioned below the breast pumping table. The table is sized to hold a breast pump, and has a ridge extending from a top of at least a part of its perimeter. The table further defines two openings so that a part of a bottle or breast pumping shield can pass through, so as to provide access to a bottle resting on the bottle shelf below. In other embodiments, the bottles may rest on the table, omitting a bottle shelf below. Each of the breast pump table and bottle shelf are connected to a support, which in turn is connectable to a forward-leaning chair. In other embodiments, the assembly may comprise only the breast pumping table, and bottles can be positioned thereon, instead of on a shelf below.

In another aspect, a forward-leaning breast pumping chair is provided. The chair has a center post, a seat and head rest attached thereto, and a base. The center post is angled forwardly relative to the base so that when a user sits on the seat, they are positioned to be leaning forward relative to the base and the flat ground that the base rests on. The chair further includes a breast pumping assembly attached to the center post. The assembly comprises a breast pumping table and a bottle shelf positioned below the breast pumping table. The table is sized to hold a breast pump, and has a ridge extending from a top of at least a part of its perimeter. The table further defines two openings so that a part of a bottle or breast pumping shield can pass through, so as to connect to a bottle resting on the bottle shelf below. Each of the breast pump table and bottle shelf are connected to a support, which in turn is connected to the forward-leaning chair.

DETAILED DESCRIPTION

Figure 1:
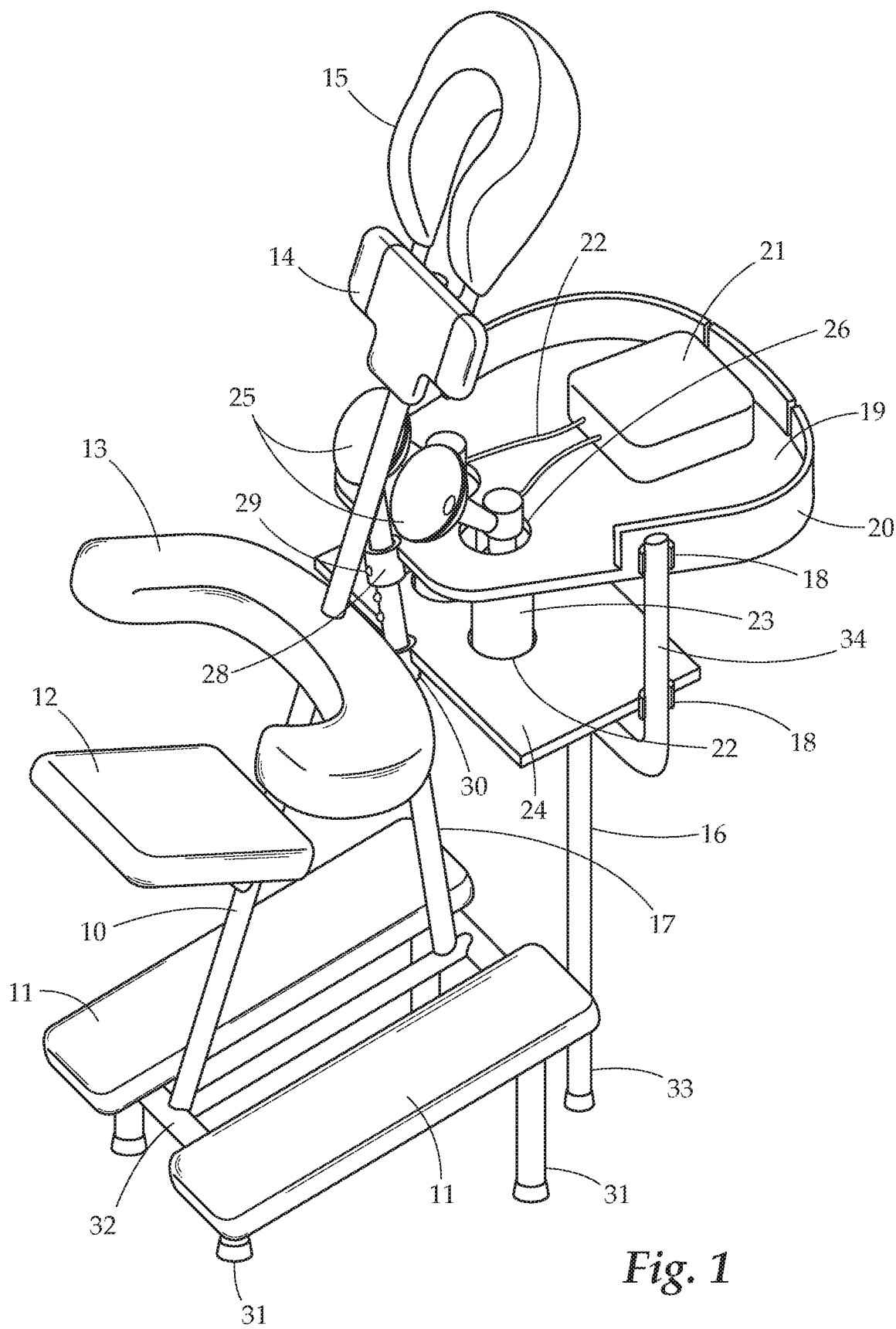
FIG. 1 provides a perspective view of an embodiment of a breast pumping chair.

The detailed description set forth below in connection with the appended drawings is intended as a description of presently preferred embodiments of the invention and does not represent the only forms in which the present disclosure may be constructed and/or utilized. The description sets forth the functions and the sequence of steps for constructing and operating the invention in connection with the illustrated embodiments.

Generally, the present disclosure concerns a breast pumping system which allows a mother who is pumping breast milk to rest in a comfortable and effective pumping position. The system involves a forward-leaning chair which angles the body forward, and allows the mother's front to rest on various supports. A breast pump table is positioned ahead of the mother's breasts, which can be connected to bottles and a breast shield (also referred to as a funnel, or flange). The mother, once positioned on the chair, can connect the breast shields and activate the pump, allowing her to pump in an ideal position without holding the breast milk bottles with her hands. The breast pumping system disclosed utilizes gravity (by the forward-leaning) as well as optimal body positioning and comfort to allow for maximum pumping success.

The breast pumping system may be integrated with a forward-leaning chair, or may be formed as an add-on to existing forward-leaning chairs, such as a massage chair. In preferred embodiments, various components including the breast pump table, support pads, and the like, may be adjustable in position to accommodate for both different sized bodies, and also to accommodate for the change in an individual mother's postpartum body, which can change significantly.

In one embodiment, a breast pump table may be positioned on the chair at approximately breast-level when a user is resting on the chair. This puts the breast pump in an easily accessible position for the mother. Various structures may be employed to aid in holding the breast shields, and bottles connected thereto, to the breasts. For example, the table and/or entire assembly may shift backwards and forwards as well as up and down, left and right relative to the chair to engage with the breast shields of the bottle with the breasts. This allows for hands-free operation, increasing relaxation and comfort. In one embodiment, the chair may have a breast holder formed as a panel with breast-sized openings. The breast shields, which seal to the breasts and funnel to the bottles, may seat in these openings, with the bottles on the opposite side of the panel. A user may lean forward such that the breasts engage with the breast shields, and as supported by the chair, is positioned in a relaxing and physiologically optimal position for pumping and breast milk expression. In many embodiments, the position and orientation of the breast holder panel with respect to the chair may be adjustable in numerous directions to optimize comfort to the user, and to adjust to the mother's changing post-partum body. Other solutions to hold the shields to the breasts may include a strap, special bra designed for such a use, securing the bottles in position, and the like.

In certain embodiments, depending on configuration, the breast pump table may include a bottle shelf which positions the pump above or below the bottles which rest on the shelf. In various configurations, this may yield a more accessible and comfortable experience for the user, making the pump and bottles more accessible and less prone to spillage and tipping. In certain embodiments, the breast pump table may have a perimeter ridge to contain spills and prevent accidental sliding off of the breast pump and optionally bottles placed thereon. In another embodiment, the bottle shelf may have a perimeter ridge. In yet another embodiment, the bottle shelf may have one or more holders to hold bottles in place securely.

In one embodiment of the forward-leaning breast pumping chair as a whole, typical components include a center post which angles forward from a base or feet. A seat is attached to the post and similarly angled forward, causing the user to be drawn towards the post by gravity to a forward leaning position. In some embodiments, a safety belt or similar strap may be included to hold the user to the seat, abdomen rest, or to another part of the chair and/or table. This provides added security in case the user falls asleep and generally encourages relaxation. A chest rest and optional shin rests are attached to the post to support legs and chests of the user. Further, a head rest is positioned on the post to allow a user to rest their head comfortably. The breast pumping chair may also include arm rests and an abdomen rest to increase comfort, and thus relaxation, for the breast-pumping user. In addition to these components, a table for holding the breast pump, and an optional breast holder for supporting and positioning the breasts may also be included on the chair, allowing a seated mother to easily pump breast milk by placing her breasts appropriately, and connecting to a pump, which may be resting conveniently on the table. In further embodiments, the table and/or breast holder may further be supported by a foldable arm which allows them to fold or pivot relative to the massage chair so as to move out of the way, to reduce space and improve access (sitting and standing) from the chair.

In some embodiments, an existing forward-leaning massage chair may be modified to have a breast pumping system including an attached breast pump table and/or a breast holder to support and position the breasts. The table and/or breast holder can be removably attached to the forward-leaning massage chair and once attached, may be adjustable in one or a plurality of axes. Connection may be achieved in any manner, including but not limited to snapping on, clamping, connectors, pins, bolts, screws, adhesives, and the like. In further embodiments, as noted above, the table and/or breast holder may further include a foldable arm which allows them to fold or pivot relative to the massage chair so as to move out of the way, to reduce space and improve access (sitting and standing) from the chair.

Figure 2:
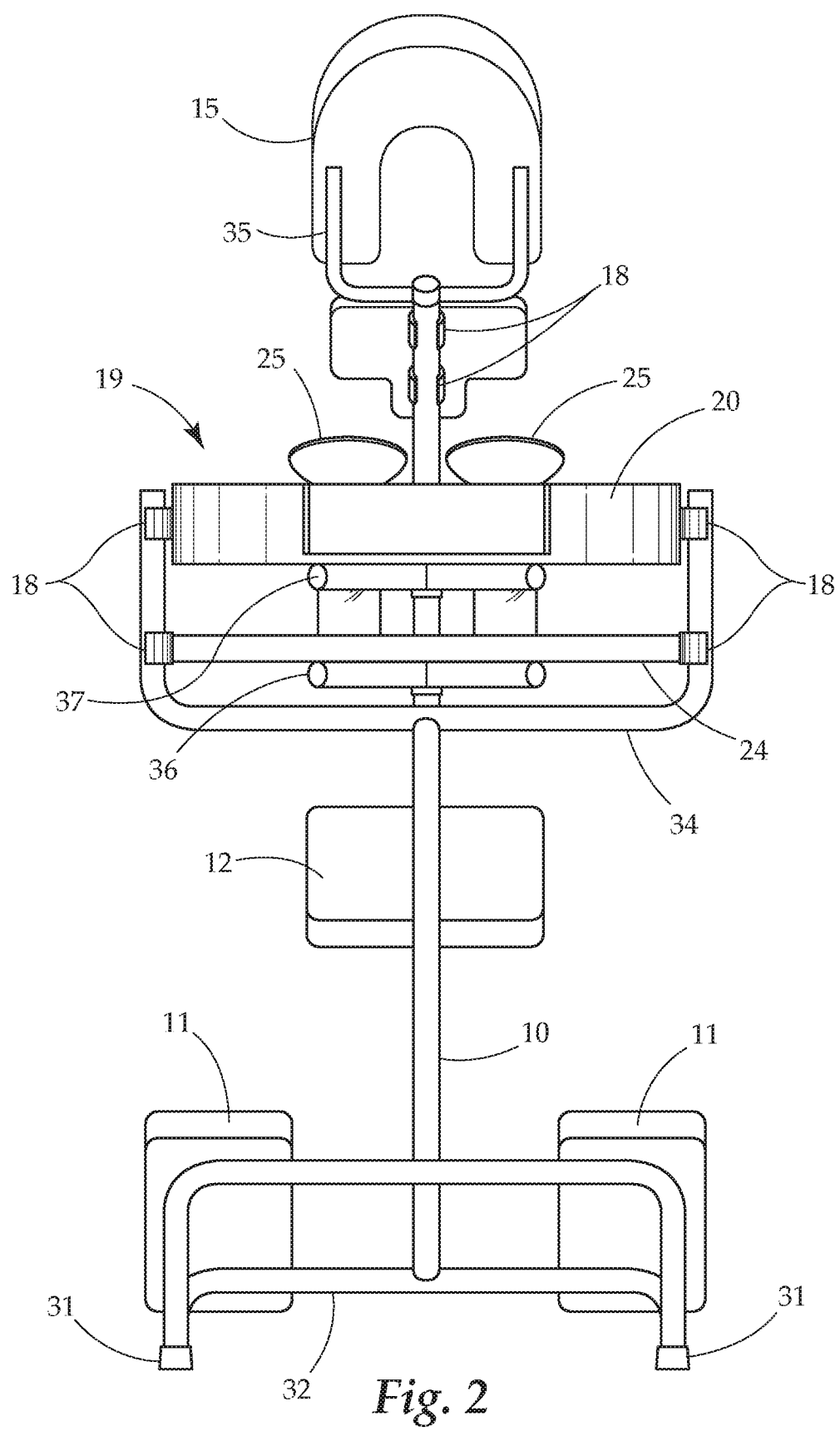
FIG. 2 provides a frontal view of the embodiment of FIG. 1.
Figure 5:
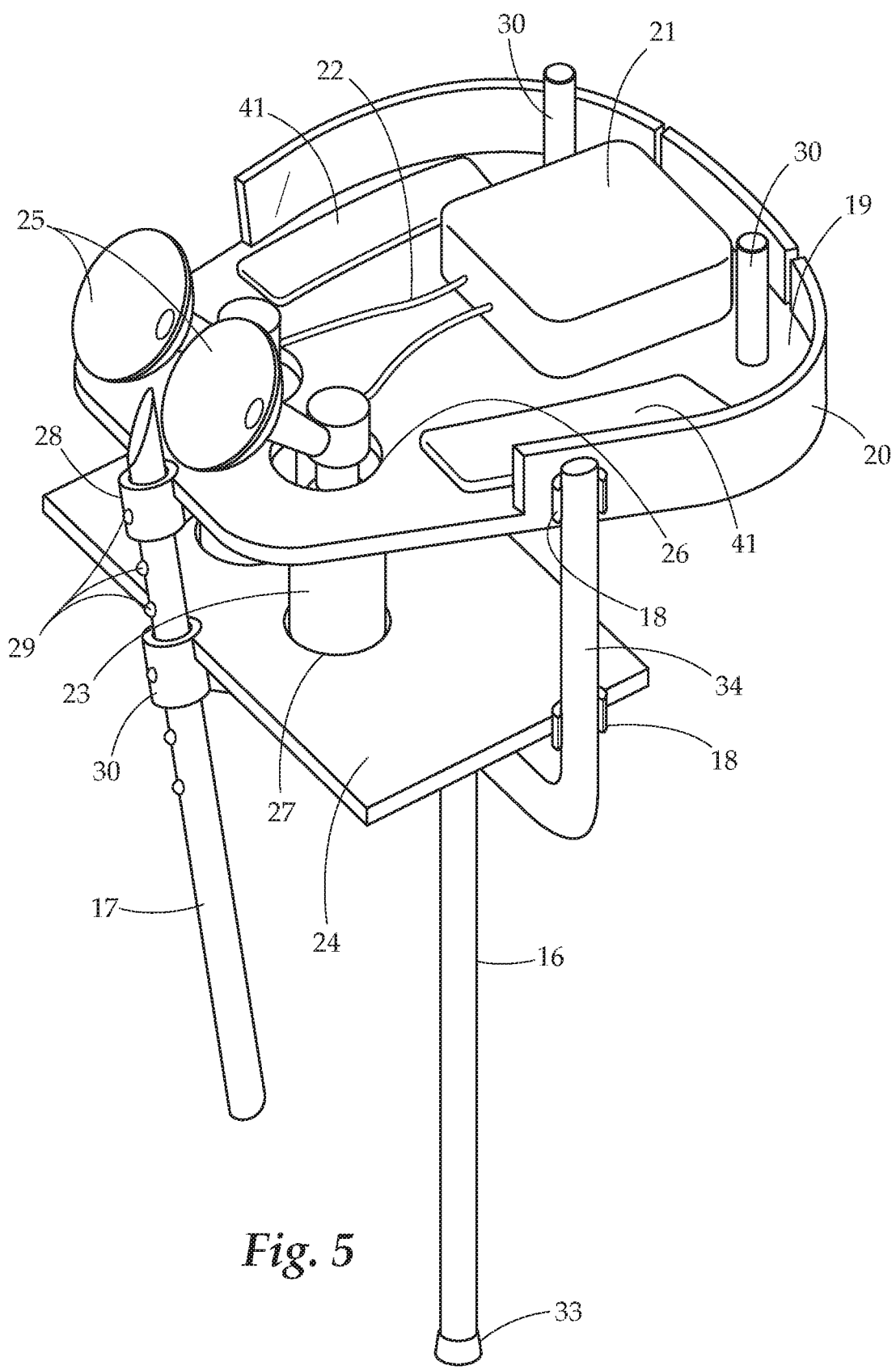
FIG. 5 provides a perspective view of an embodiment of breast pumping components of the breast pumping system.
Figure 10:
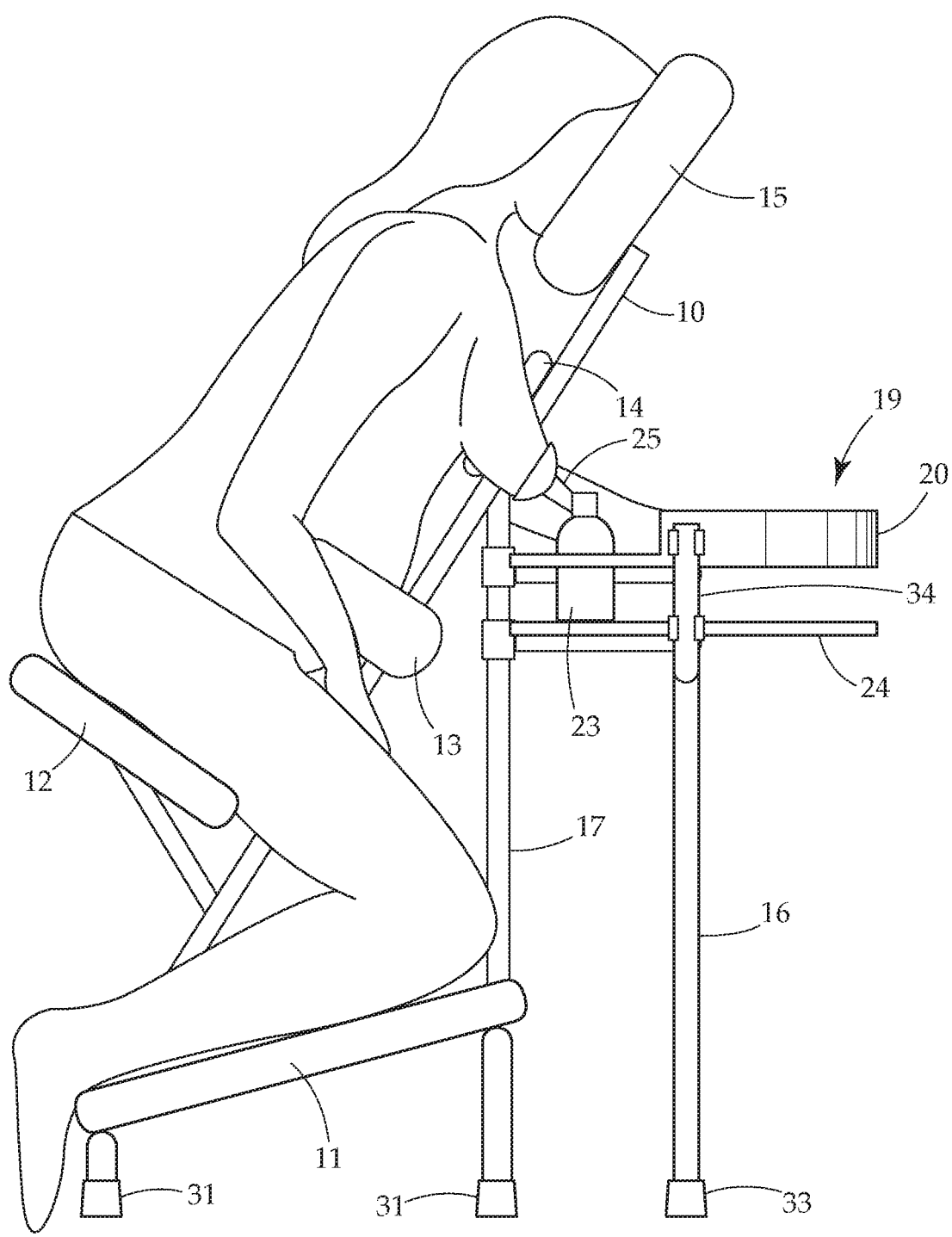
FIG. 10 provides a side view of an embodiment of the breast pumping system in use.

Turning now to FIGS. 1, 2, and 5, perspective and front views of an embodiment of the breast pumping system integrated into a forward-leaning chair is provided. The chair is based around a central post 10 which angles a seat 12 forward relative to a base 31, 32 resting on the floor. In certain embodiments the base 31 may have feet which are made to contact the floor. In other embodiments (not shown) the base 31 may have casters, allowing easy movement of the chair along the floor. Casters may be locked and/or retracted to safely hold the chair in place when being used. A seat 12, shin rests 11, abdomen support 13, chest support 14, and head rest 15 all provide support to a person's body resting in the chair. These may each be adjustable in position and orientation in height, angle, and in some cases, lateral direction, in certain embodiments, so as to maximize comfort and relaxation to the user. In FIG. 10, the forward-leaning chair and breast pumping system can be seen in use by a user who is pumping breastmilk.

In this view, the breast pumping components are built in to the chair, although as noted above, the components may be removably attached in other embodiments. As shown in the embodiments of FIGS. 1, 2, 5, and 10, a support bar 17 extends from the base 31, 32 to the central post 10. A breast pump table 19 and bottle shelf 24 are connected to this bar 17 via connectors 28 and 30, which surround the bar 17 and are slideable along it. In this embodiment, the connectors 28, 30, and in turn the pump table 19 and bottle shelf 24, can be secured in place by pins 29 passing through an aperture in each connector 28, 30. Adjustment is achieved by pressing on pin 29 so that it does not extend through the aperture, and then sliding connectors 28, 30 along support bar 17. Other adjustment, such as distance from center post 10 may be possible as well via, for example, a telescoping shaft (not shown). Of course, other structures for holding the connectors in place to the bar 17 may be used without straying from the scope of this invention.

The breast pumping components are supported by a support 16 having a foot 33 resting on the ground. In other embodiments, a caster or casters may replace foot 33. In another embodiment, the breast pumping shelf 24 and table 19 may be supported by one or more support 16 legs having casters at their end, so that the shelf 24 and table 19 can be easily moved around a floor by the casters (not shown). In other embodiments, connection to the center post 10, whether directly or indirectly, and permanently or removably, may be sufficient to support the breast pumping components. Bottle shelf 24 connects to an upright 34, supported by cross bar 34, via clip 18. The bottle shelf 24 in this embodiment also includes a bottle holder 22 formed here as a recess in the surface of the bottle shelf 24. In operation, the bottle 23 can sit into the bottle holder 22 recess to increase stability and limit accidental spillage of the bottle or disconnection of the shield 25 from a breast.

Breast pump table 19 is designed to hold a breast pump and also in most embodiments, to provide convenient placement of breast pumping shields 25 which are connected to bottles 23. An angle, height, position, and direction of the breast pump table 19 can be adjusted for maximum comfort. In one embodiment, a ball and socket joint may be used to connect various components to allow for multi-directional adjustment. In the embodiment shown, the breast pump table 19 comprises a perimeter ridge 20 which operates to prevent items from sliding off the table 19, and optionally to contain any spills. Further, openings 26 allow bottles held on the bottle shelf 22 below to pass through. In other embodiments (not shown) bottles 23 may rest on the breast pump table 19 instead of on a different shelf. Breast pump 21 rests on the breast pump table 19, having tubes 22 drawing a low pressure connected to the shields 25, which cause the pumping action. While shown permanently connected to the elements of the chair, it should be understood that in other embodiments, the breast pumping components (table 19, shelf 24) may be removably connected to the chair, and in further embodiments may be movable relative to the chair while connected.

Bars 37 and 36 are used in this embodiment to support breast pump table 19 and bottle shelf 24, respectively. These bars connect to the connectors 28, 30 to provide strength to the table 19 and shelf 24. Head rest 15, in this embodiment, is connected to an end of the center post 10 by a support bar 35. As assembled, the breast pumping chair and components allows for a mother to be optimally positioned to maximize pumping effectiveness by facing forward causing gravity to assist in milk expression, and to be in a very comfortable and relaxed position, reducing stress and relaxing the body leading to improved milk expression.

Figure 3:
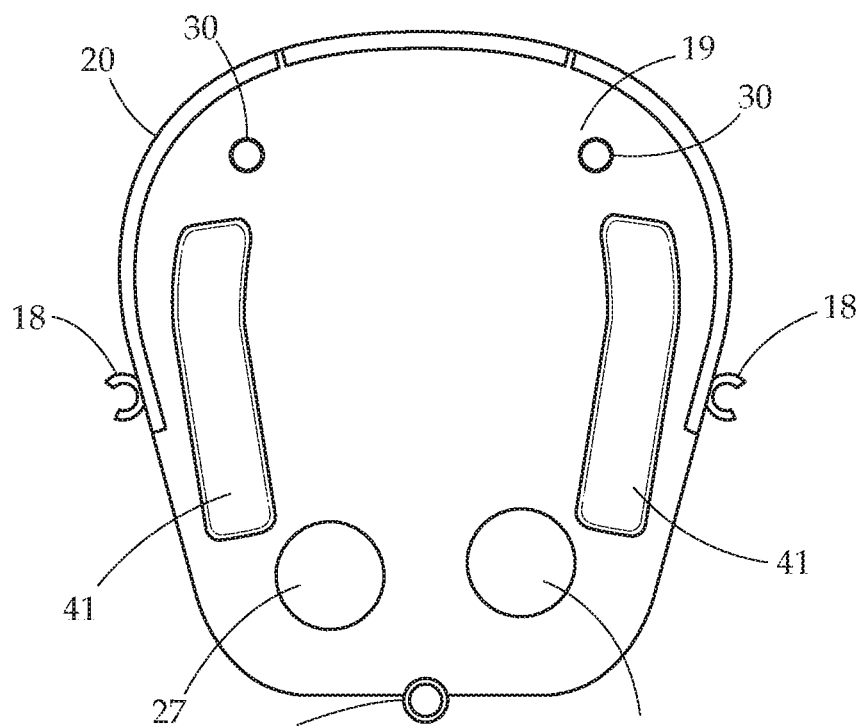
FIG. 3 provides a top view of a breast pumping table attachable to a forward-leaning chair.
Figure 4:
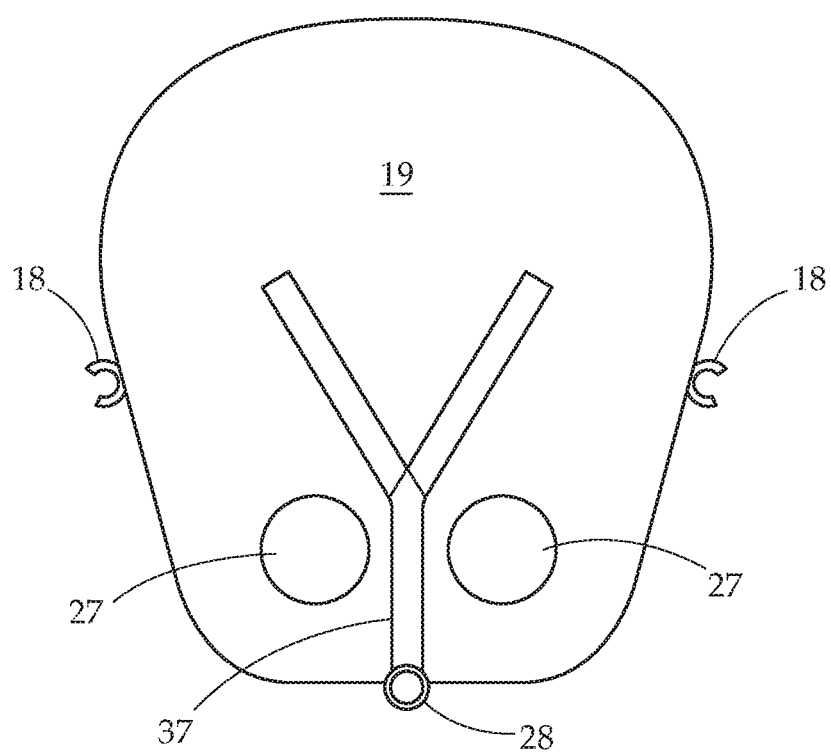
FIG. 4 provides a bottom view of a breast pumping table attachable to a forward-leaning chair.

FIGS. 3 and 4 provide a view of an embodiment of the breast pumping table which may be removably or permanently attached to the forward-leaning chair. Table 19 has ridge 20 around its perimeter. Clips 18 allow, in this embodiment, connection to uprights of the breast pump component assembly. Of course, other modes of connection, whether permanent or removable are within the scope of this disclosure. In this view, the table 19 includes arm rests 41, which provide a padded and/or contoured area for a user to rest their arms. Table 19 also includes handles 30 for a user to hold onto, providing comfort and allowing a user to adjust body position and/or shield 25 position by pulling and otherwise manipulating the handles. Openings 26 allow the bottle and/or shields or parts thereof to pass through the table 19. Connector ring 28 allows connection to a support such as bar 17. As with clips 18, any structure may be used to permanently or removably connect the table 19 to the forward-leaning chair. In this view, a 'Y' shaped bar 37 connects to connector and supports the table 19. A handle (not shown) may be positioned anywhere on the breast pumping table 19 and/or on the bottle shelf 24 to aid in movement of the table as well as the entire chair assembly. Further, table 19 and shelf 24, in certain embodiments, may have a pivotal connection allowing them to fold upward or downward into a compacted position. This hinged connection may be at the connector ring 28, or the table 19 and shelf 24 may be hingedly connected to the chair at, for example, center post 10.

Figure 6:
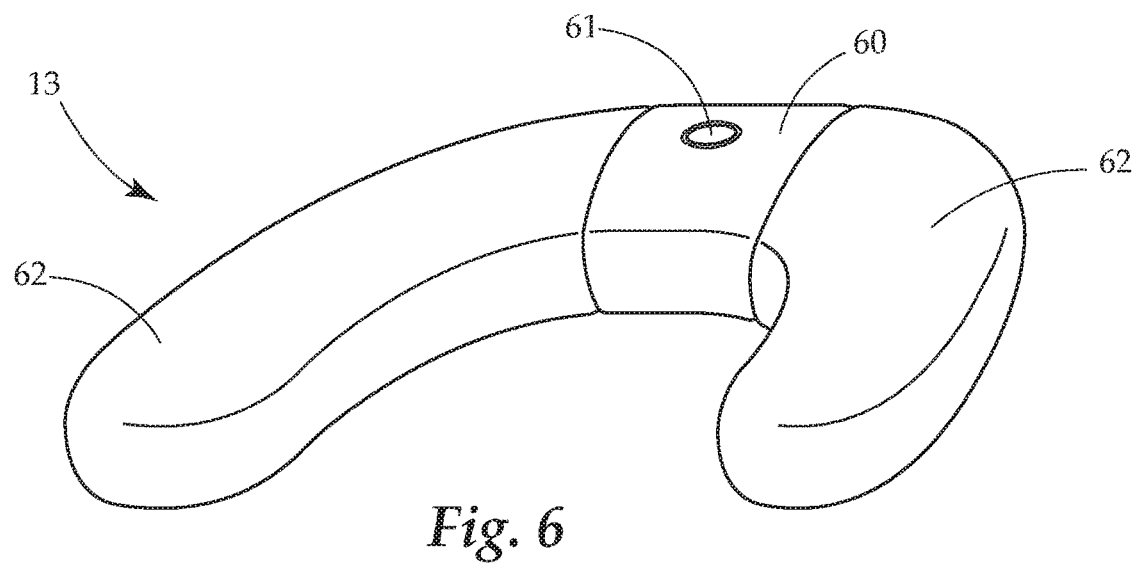
FIG. 6 provides a perspective view of an embodiment of an abdomen rest for the forward-leaning chair.
Figure 7:
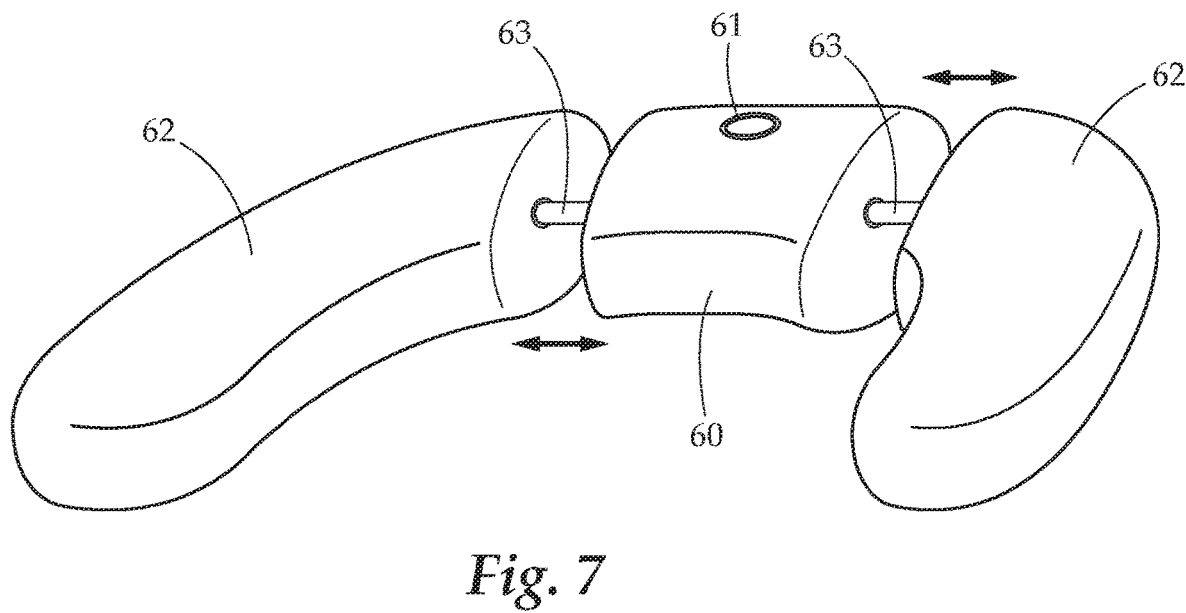
FIG. 7 provides a perspective view of an embodiment of an abdomen rest for the forward-leaning chair.

FIGS. 6 and 7 show an embodiment of the abdomen rest of the forward-leaning chair. In this embodiment, abdomen rest 13 has a base 60 and arms 62 which are shaped to wrap around an abdomen of a user. In certain embodiments, the abdomen rest may be padded. The base 60 has an opening 61 through which a center post may pass. Other modes of connection of the base 60 to the forward-leaning chair may also be employed, such as a clip, clamp, or permanent welded or molded connection, among others. As shown in FIG. 7, the arms 62 of the abdomen rest 13 are adjustable in position. Arms 62 connect to shaft 63 which can allow the arms to extend outwardly and to optionally rotate about an axis of the shaft 63. This allows the abdomen rest 13 to be maximally adaptable for varying sized mothers.

Figure 8:
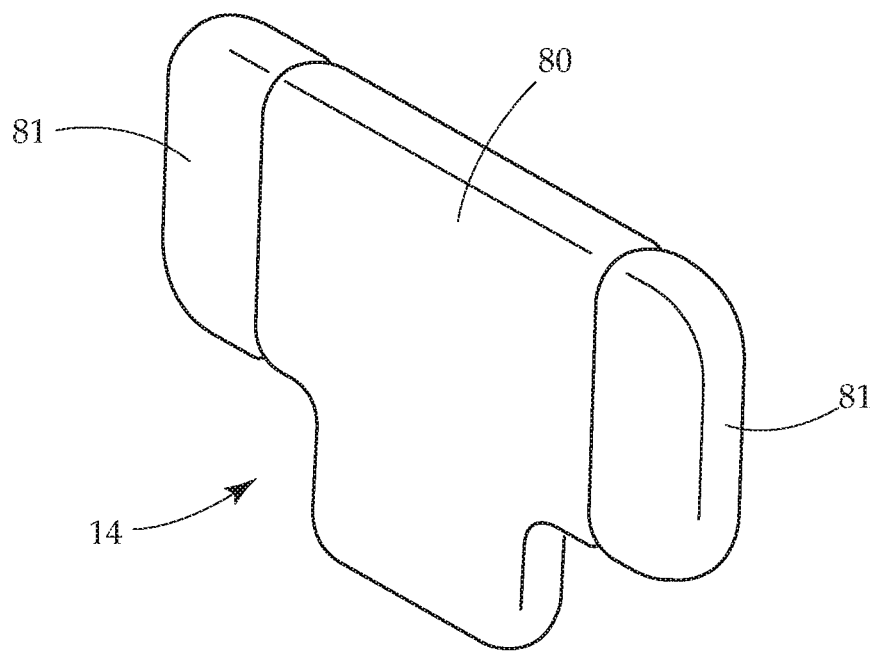
FIG. 8 provides a perspective view of an embodiment of a chest rest for the forward-leaning chair.
Figure 9:
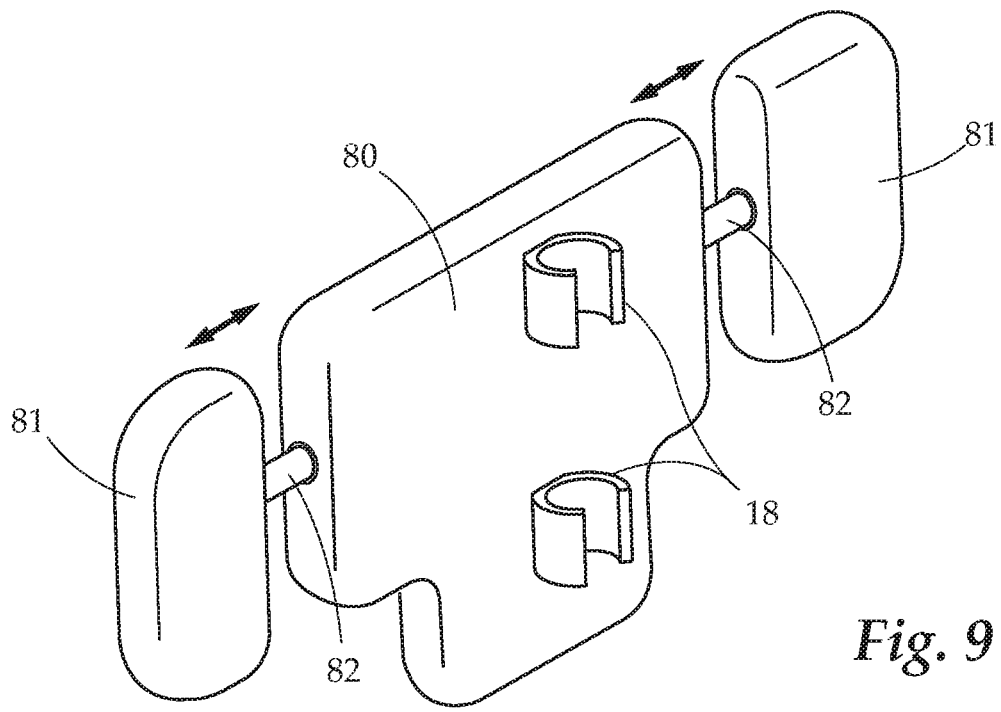
FIG. 9 provides a perspective view of an embodiment of a chest rest for the forward-leaning chair.

FIGS. 8 and 9 show an embodiment of a chest rest of the forward-leaning chair. The chest rest 14 has a base 80 which can be connected to the forward-leaning chair, as well as arms 81 extending from opposite sides of the base 80. On the rear of the base, in this embodiment, are two clips 18 which may removably and adjustably attach to a center post of the chair. Other modes of connection of the base 80 to the forward-leaning chair may also be employed, such as a hole through the base 80, clamp, or permanent welded or molded connection, among others. As shown in FIG. 9, the arms 81 of the chest rest 14 are adjustable. Arms 81 connect to shaft 82 which can allow the arms 81 to extend outwardly and to optionally rotate about an axis of the shaft 63. This allows the chest rest 14 to be maximally adaptable for varying sized mothers. Other elements of the chair may have structure like this to allow them to be similarly adjustable.

Figure 11:
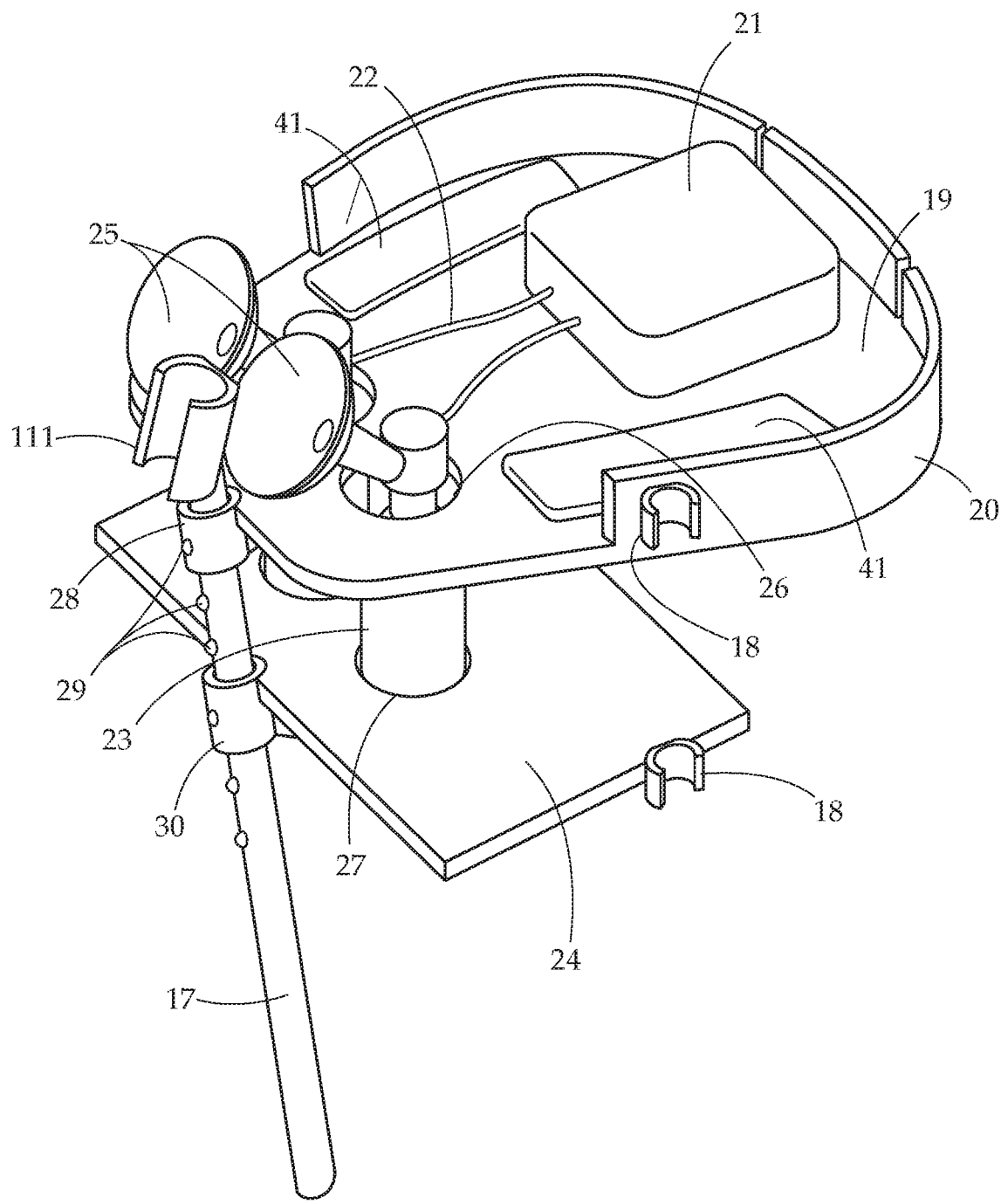
FIG. 11 provides a perspective view of breast pumping components of the breast pumping system.

FIG. 11 provides a view of a removable embodiment of the breast pumping system, which may be attachable to an existing forward-leaning chair such as a massage chair. Here, the previously described components including the breast pumping table 19 and bottle shelf 24 below are connected to a support 17. The support 17 is shown here as a bar which allows for relative movement along the bar of the table 19 and shelf 24. This bar 17 may connect to a forward-leaning chair such as a massage chair, or may be free at its end without connection. In certain embodiments, bar 17 may removably connect to the forward leaning chair by, for example, clipping into the base, having a foot which rests on the base, a frictional connection to the base, and the like. However, in other embodiments, any sort of support may be used without straying from the scope of the invention. Notably, a connector, shown here as a robust clip 111 allows connection between the breast pumping system to the forward-leaning chair. In different embodiments, an optional support leg, such as leg 16 as shown in other figures, may also be attached to the shelf 24 and table 19 to provide additional support. As such, an existing forward-leaning chair may be used as a breast pumping chair system allowing a user to rest on the forward-leaning chair and comfortably pump breast milk.

Figure 12:
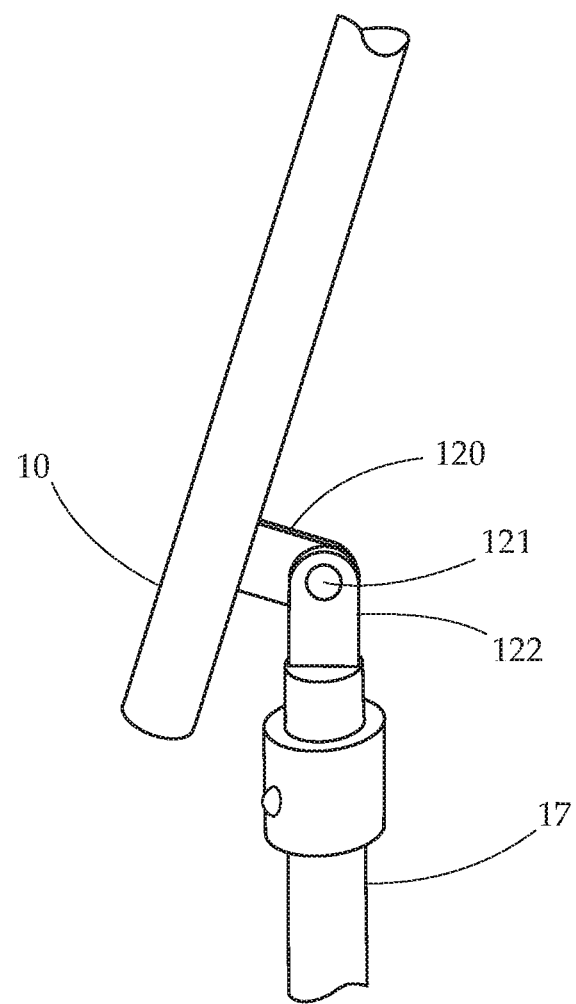
FIG. 12 provides a detail view of components of the breast pumping system.

FIG. 12 provides a view of a hinged connection between the center post 10 and support 17. In such an embodiment, the hinged connection allows for adjustment of the breast pumping table 19 and/or shelf 24, and thus adjustments of any components thereon. This may be particularly advantageous to bring the breast shields 25 in optimal position relative to the breasts of the breast pumping mother to achieve a good seal and thus effective pumping. In this view, two stems 120, 122 extend from the center post 10 and the support 17, respectively. These stems 120, 122 are pivotally movable about hinge 121. In a related embodiment, Stem 120 may be joined to a connector (not shown) such as clip 111 of FIG. 11, to allow for removable connection of the breast pumping system to a forward-leaning chair.

Figure 13:
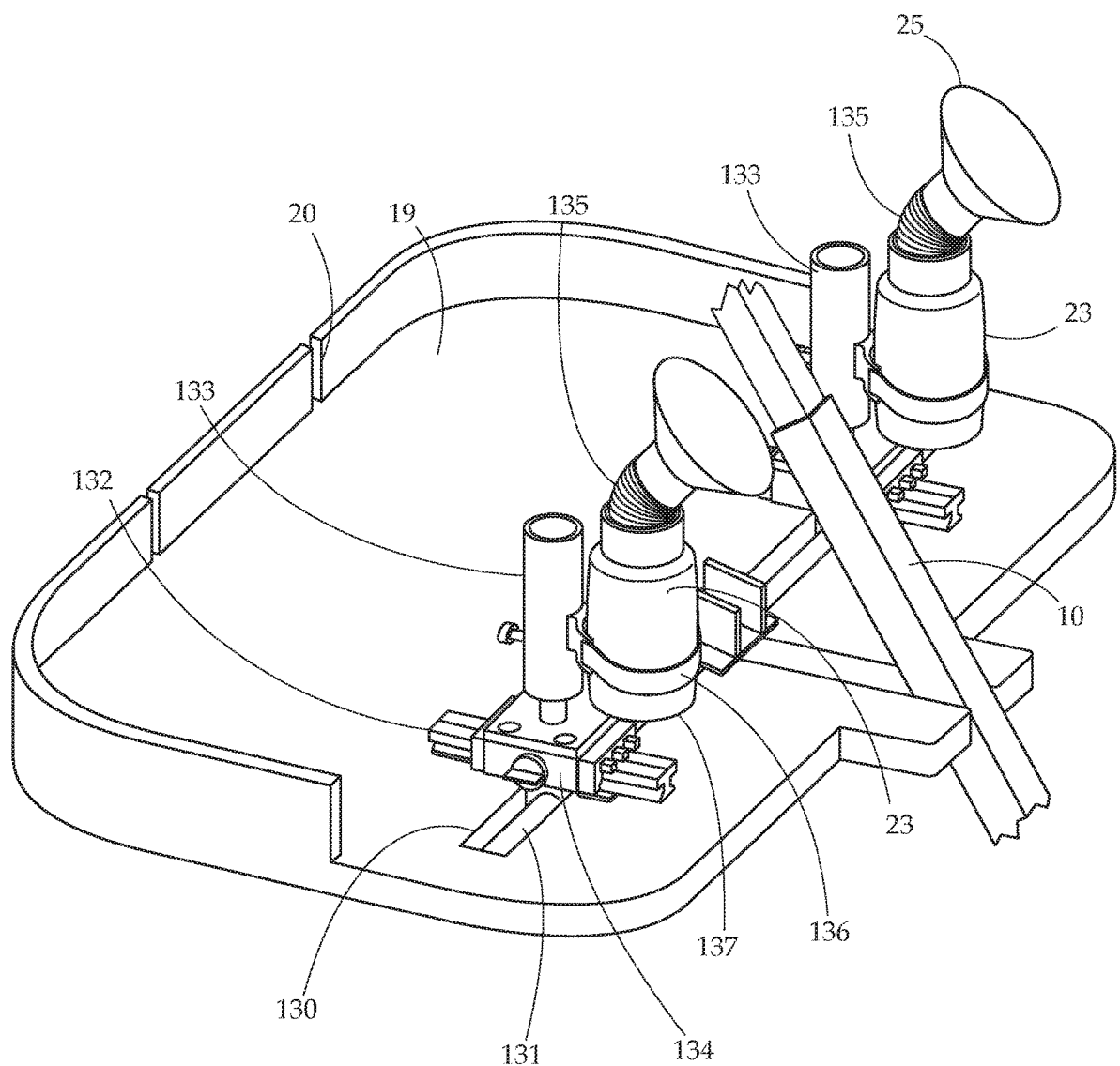
FIG. 13 provides a view of another embodiment of the table of the breast pumping system.

FIG. 13 provides a detail view of another embodiment of the table of the breast pumping system. In this view, the bottles 23 are connected to the table by way of a multi-directional adjustable bottle holder base assembly. The adjustable base assembly is formed of a base 134 which can move left to right, forward and back along a horizontal plane. The base 134 connects to the table 19 at a slide bar 131 which is set into a channel 130 of the table 19. Of course, other slideable or adjustable configurations may be used without straying from the scope of this invention. Further, the base 134 is also slidably mounted to a distance slide bar 132, which allows for adjustment of the base location forward or backward relative to a front or rear edge of the table. Extending upward from the base 134 is a bottle holder column 133. The column 133 is pivotally connected to the base 134 so that it can rotate about its major axis, which in turn allows the bottle 23 attached thereto to pivot. Other configurations other than a column may of course be used to connect the bottle 23 to the base 134. A bottle holder 137 is connected to the column 133. The bottle holder may be any structure which allows the bottle to be held in place. In this embodiment, the bottle holder 137 has a base on which the bottle 23 rests, and a strap 136 which holds the bottle tightly in place. A clamp holds the bottle holder 137 to the column 133. This clamp can be loosened to move the bottle holder 137 upwards and downwards. As with the other components, the bottle may be held by various structures which allow upward and downward movement and connection to the column 133 without straying from the scope of this invention. The breast pump table 19 further comprises a perimeter ridge 20 which operates to prevent items from sliding off the table 19, and optionally to contain any spills. In the view shown, two slits are present on the ridge which allow passage of cords such as power cords for the breast pump. These ridges may extend all or part of the height of the ridge.

Figure 14:
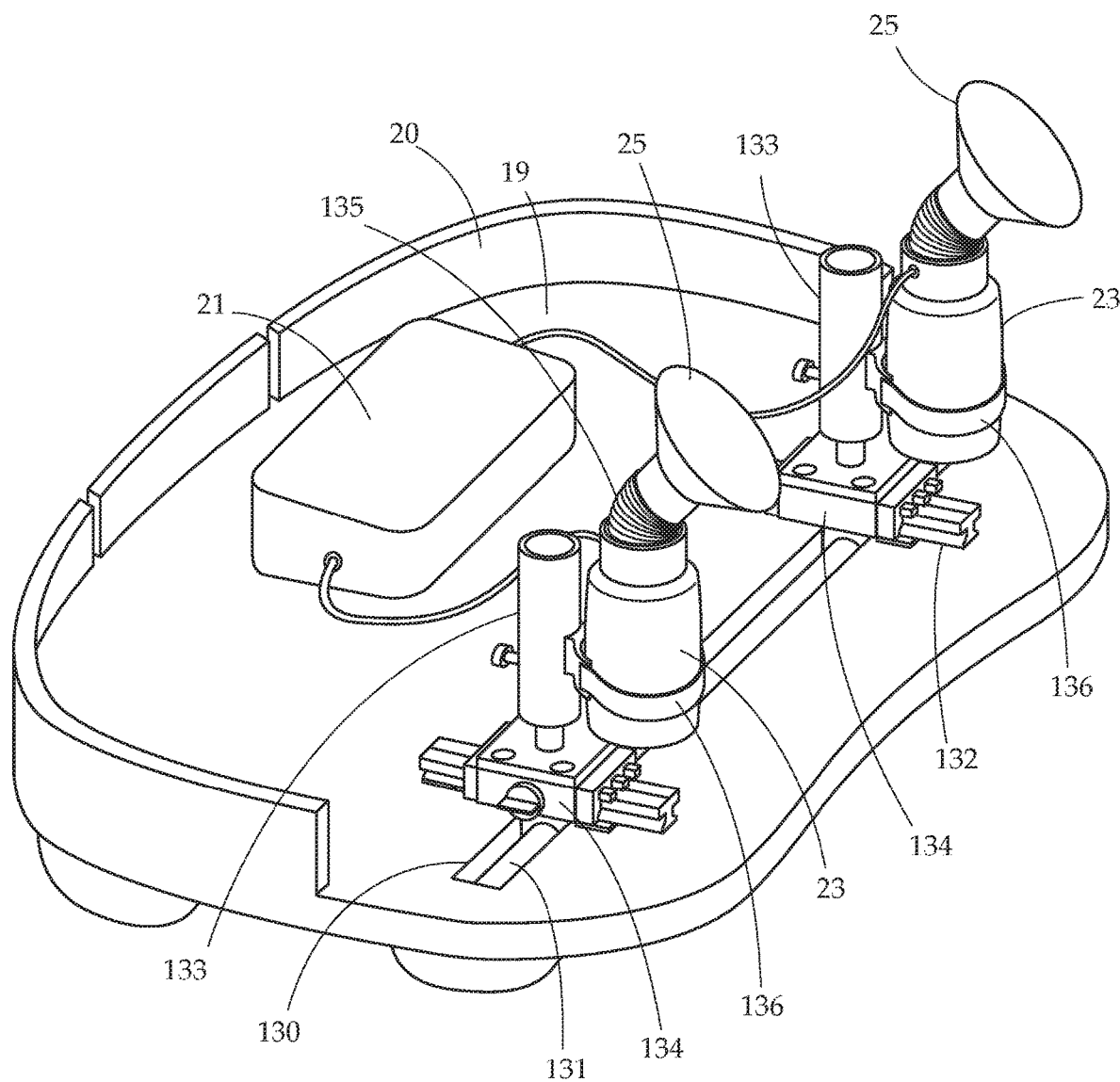
FIG. 14 provides a view of yet another embodiment of the table of the breast pumping system.

FIG. 14 provides a view of an embodiment of the breast pumping table which is separate from the chair. This view contemplates a stand-alone table platform on which a breast pump 21 and bottles 23 may rest. This allows for a breast pumping mother to comfortably relax while pumping, rather than having to uncomfortably hold the bottles and have to activate/operate the pump. In the particular view shown, the table 19 is formed as a platform or surface which can rest on a user's lap. In other embodiments, the table 19 may have foldable legs to allow for lap and/or table leg-supported table operation. A movable assembly for the bottles is shown integrated into the table 19, as in FIG. 13. However, this is not necessarily required for the stand-alone table embodiments. In lap based embodiments, pads or other structures may be used to elevate the table and make it comfortable. As noted herein, pumping effectiveness is greatly increased by optimizing body positioning, relaxation, and comfort. In certain embodiment, the table may incorporate a head rest (not shown) similar to that of FIG. 15.

Figure 15:
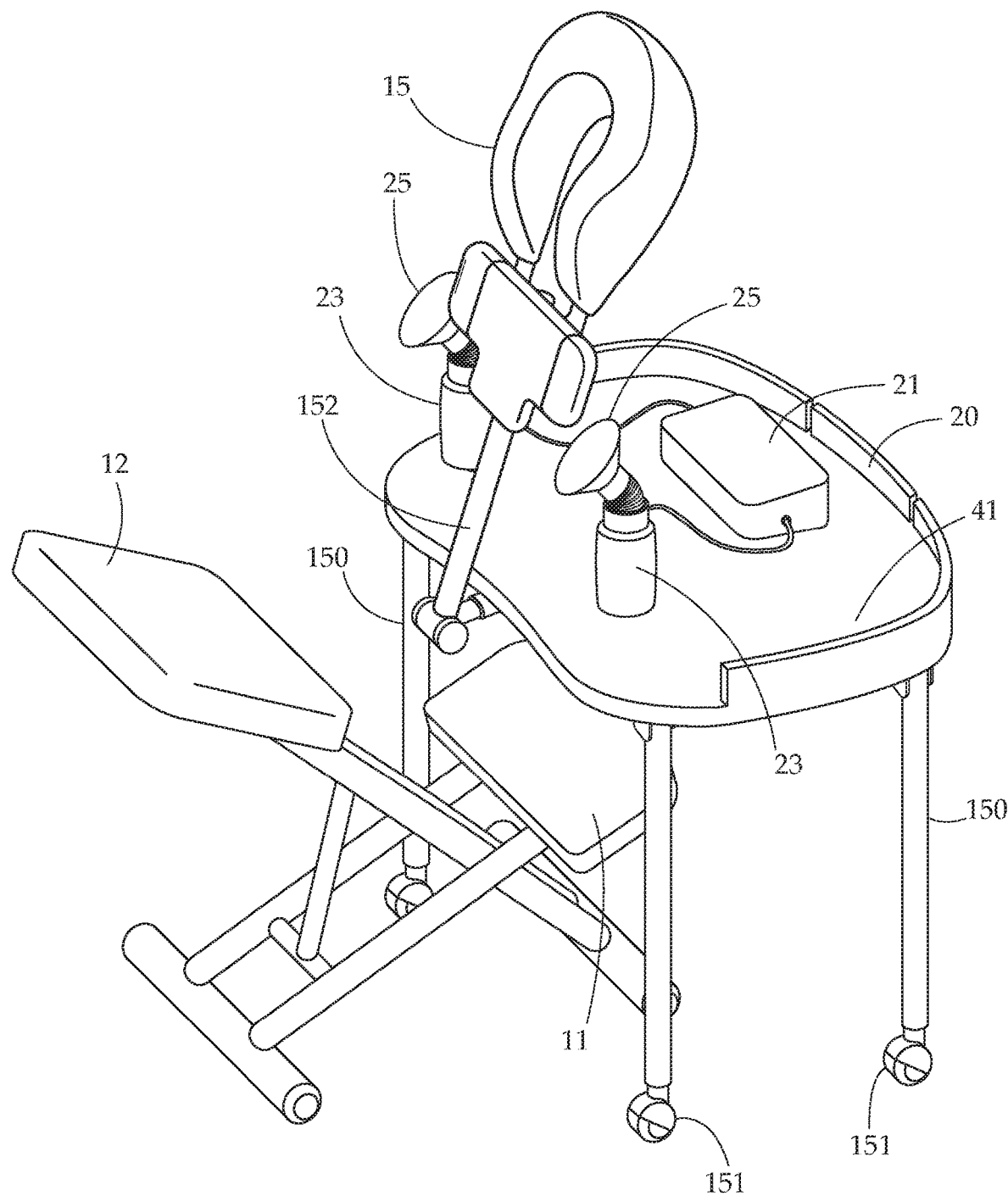
FIG. 15 provides a view of still embodiment of the table of the breast pumping system.

FIG. 15 shows another embodiment of a stand-alone pumping table which holds the breast pump 21 and bottles 23. Similarly to the embodiment of FIG. 14, in this view, the table 19 supports the breast pump 21 and bottles 23 and provides an optimal positioning of the components for effective pumping. The table 19 further has a head rest 15 which extends from a top or bottom surface, or side. In this embodiment, a shaft 152 provides a hinged connection to the table. As such, the head rest 15 can be adjusted in position, and can also be folded away for compact storage of the table. Or course, any connection structure may be used to connect the head rest to the table. The head rest 15 being connected to the table 19 may be applied to any of the other embodiments disclosed herein, such as that of FIG. 14 among others. This view of the table shows a forward leaning chair having a forward-angled seat and a shin or knee rest 11, allowing the pumping user to comfortably lean forward during the pumping. However, it should be understood that any chair or other seating arrangement, or even a standing forward-leaning configuration may be used without straying from the scope of the invention. Legs 150 extend from the bottom of the table 19. Ends of some or all of the legs 150 may have lockable casters 151 to facilitate movement of the table. In certain embodiments, the legs may be adjustable in length to change a height of the table. Further, the legs 150 may be hingedly connected to the table, to allow them to fold up for convenient storage, transportation, and optional lap use.

While several variations of the present disclosure have been illustrated by way of example in preferred or particular embodiments, it is apparent that further embodiments could be developed within the spirit and scope of the present disclosure, or the inventive concept thereof. However, it is to be expressly understood that such modifications and adaptations are within the spirit and scope of the present disclosure, and are inclusive, but not limited to the following appended claims as set forth. As noted, the forward-leaning feature of the inventive system allows for optimal breast milk expression.

What is claimed is:

1. A breast pumping assembly comprising:
   a breast pump table sized to receive a breast pump;
   a forward-leaning chair removably connected to the breast pump table by a support extending between the breast pump table and the forward-leaning chair; and
   a bottle holder engaged with the breast pump table and operable to hold at least one bottle for receiving pumped breast milk, the bottle holder engaged with the table by an adjustable base assembly having a base, and wherein the base is movable to adjust a position of the bottle relative to the breast pump table to accommodate differently sized users; and
   wherein the adjustable base assembly allows movement of the bottle holder in a horizontal direction, and a rotational direction;
   the adjustable base assembly further comprising a column extending from a proximal end of the base, the bottle holder pivotally connected to the column and rotatable about a major axis of the column, allowing the bottle holder to pivot in the rotational direction; and
   wherein the base comprising a distance slide bar at a distal end positioned in a channel defined by the table, the slide bar and channel allowing slideable movement of the base and the bottle holder connected to the base, to a plurality of different positions along the horizontal direction to move the bottle holder toward and away from the breast pumping table while the distance slide bar remains in the channel to engage with the table.

2. The breast pumping assembly of claim 1 wherein the adjustable base assembly is operable to move the bottle holder vertically up and down.

3. The breast pumping assembly of claim 1 wherein the bottle holder has an extending shelf on which a bottle may rest, and a strap operable to wrap about the bottle to hold it in place.

4. The breast pumping assembly of claim 1 further comprising a bottle held by the bottle holder, the bottle having a breast pumping flange connected to the bottle and in communication with an opening of the bottle, the breast pumping flange operable to receive pumped breast milk and direct the pumped breast milk into the bottle, wherein the breast pumping flange is adjustable in orientation relative to the bottle while connected to the bottle.

5. The breast pumping assembly of claim 1 further comprising a head rest connected to the table, wherein the head rest is pivotally connected to the table.

6. A breast pumping table for providing restful breast pumping comprising:
- a table sized to receive a breast pump; and
- a bottle holder operable to hold two bottles for receiving pumped breast milk;
- a bottle holder engaged with the table and operable to hold at least one bottle for receiving pumped breast milk, the bottle holder engaged with the table by an adjustable base assembly having a base, and wherein the base is movable to adjust a position of the bottle relative to the table to accommodate differently sized users; and
- wherein the adjustable base assembly allows movement of the bottle holder in a horizontal direction, and a rotational direction;
- the adjustable base assembly further comprising a column extending from a proximal end of the base, the bottle holder pivotally connected to the column and rotatable about a major axis of the column, allowing the bottle holder to pivot in the rotational direction; and
- wherein the base comprising a distance slide bar at a distal end positioned in a channel defined by the table, the slide bar and channel allowing slideable movement of the base and the bottle holder connected to the base, to a plurality of different positions along the horizontal direction to move the bottle holder toward and away from the breast pumping table while the distance slide bar remains in the channel to engage with the table.

7. The breast pumping table of claim 6 wherein the adjustable base assembly is operable to move the bottles attachable to the bottle holder vertically up and down.

8. The breast pumping table of claim 6 wherein the bottle holder has an extending shelf on which a bottle may rest, and a strap operable to wrap about the bottle to hold it in place.

9. The breast pumping table of claim 6 further comprising a head rest connected to the table, wherein the head rest is pivotally connected to the table.

10. The breast pumping table of claim 6 further comprising at least one of a pad and foldable legs attached to a bottom of the table.

* * * * *